United States Patent [19]

Bellavia

[11] 4,416,626
[45] Nov. 22, 1983

[54] METHOD FOR RECAPTURING ANTERIOR DISPLACED MANDIBULAR DISC AND ORTHOPEDIC DEVICE THEREFOR

[76] Inventor: William D. Bellavia, 511 West Ave., Medina, N.Y. 14103

[21] Appl. No.: 312,759

[22] Filed: Oct. 19, 1981

[51] Int. Cl.$^3$ .............................................. A61C 7/00
[52] U.S. Cl. ..................................................... 433/7
[58] Field of Search .................... 128/76 R; 433/7, 19

[56] References Cited

U.S. PATENT DOCUMENTS 4,239,487 12/1980 Murdock ................................ 433/7

Primary Examiner—Robert Peshock
Attorney, Agent, or Firm—Joseph P. Gastel

[57] ABSTRACT

A method of recapturing an anterior displaced mandibular disc including the steps of moving the mandible to an anterior position from its normal position to increase to the vertical height between the condyle and fossae, retaining the mandible in the anterior position to permit the mandibular disc to become displaced to a more posterior position, and periodically moving the mandible to a more posterior position in increments until it is returned to a permanent position which is anterior of its original normal position, all of the foregoing while providing sufficient clearance between the upper and lower posterior molars to permit eruption therebetween, to thereby maintain an increased vertical height. A functional jaw orthopedic device for recapturing an anterior displaced mandibular disc including a palatal body for fixed placement in the palate area in relation to the upper teeth, a mandibular body for fixed placement in the mandibular area in relation to the lower teeth, an adjustable connection between the mandibular body and the palatal body for providing relative movement in a posterior direction from an underbite position, and a clearance area between the upper and lower molars to permit eruption thereof for increasing the vertical spacing between the maxilla and the mandible in the condyle-fossae area.

14 Claims, 11 Drawing Figures

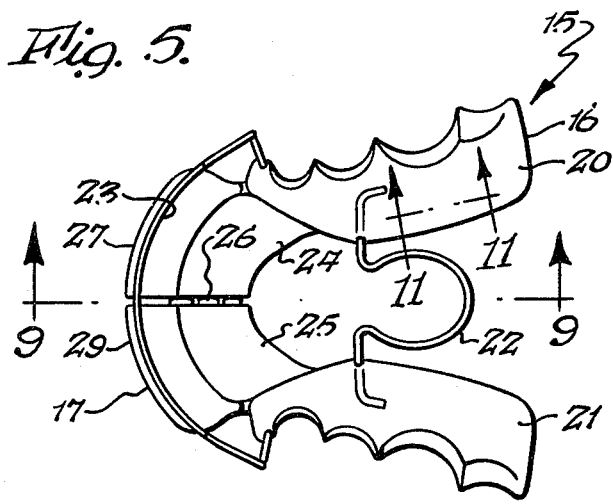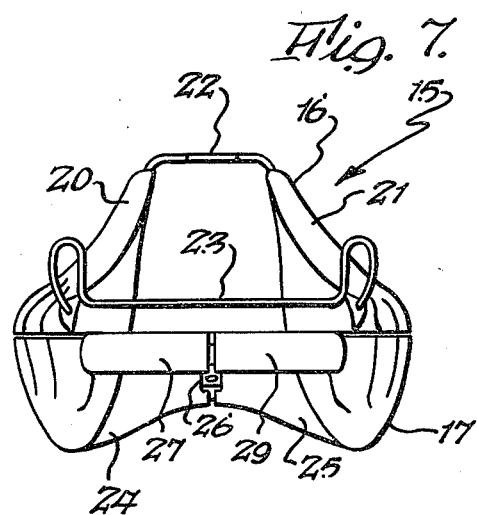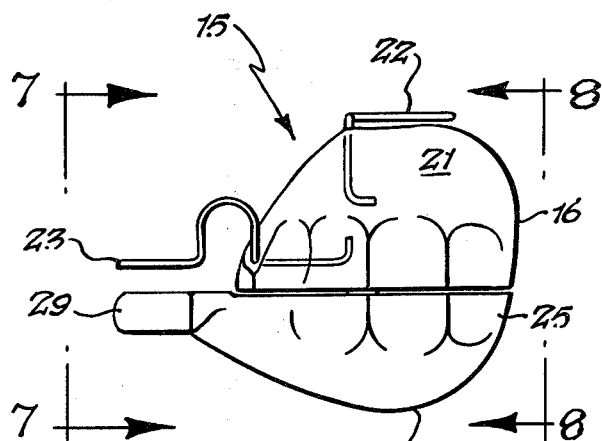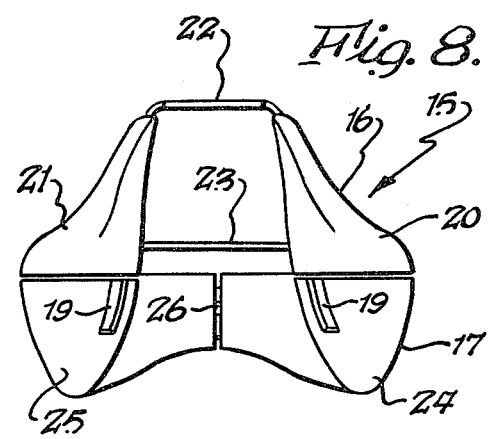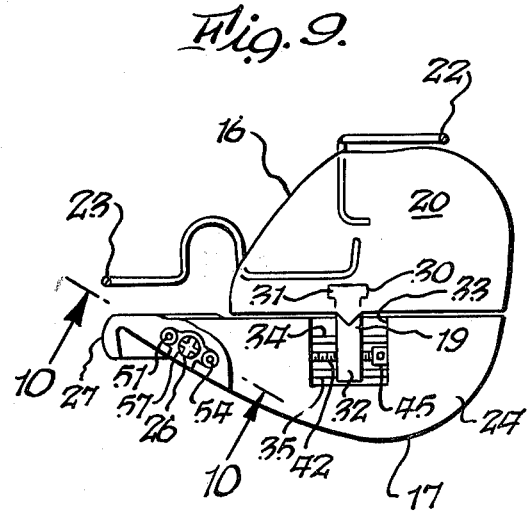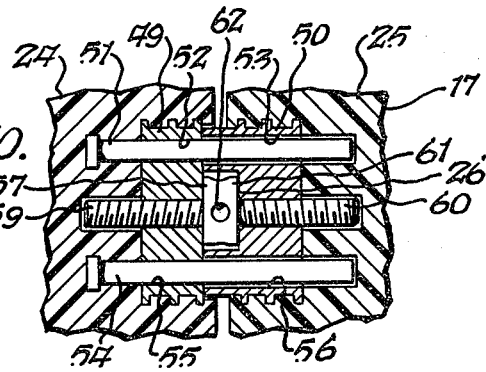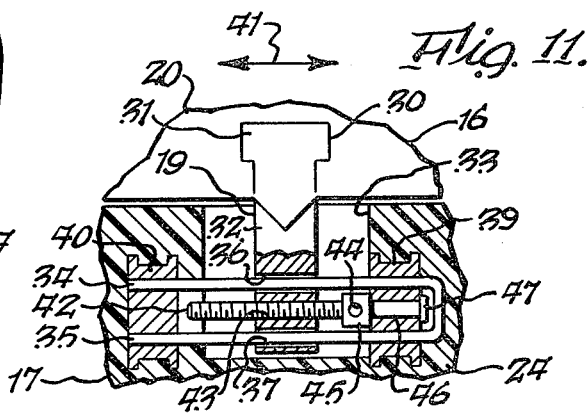

4,416,626

METHOD FOR RECAPTURING ANTERIOR DISPLACED MANDIBULAR DISC AND ORTHOPEDIC DEVICE THEREFOR

BACKGROUND OF THE INVENTION

The present invention relates to an improved method for recapturing an anteriorly displaced mandibular disc and to a functional jaw orthopedic device therefor.

By way of background, the mandibular disc is located between the condyle of the mandible and the fossae of the temporal bone. In certain instances there is a malady known as anteriorly displaced mandibular disc which is characterized by clicking of the jaws and which may ultimately result in arthritis of the condylar elements. Various methods and techniques have been utilized in the past as a treatment for the foregoing malady. However, they have all had certain deficiencies. For example, certain devices have been utilized to reposition the mandible in a more forward position. However, such devices have not had the necessary strength to accomplish the function and are subject to breakage or tissue impingement. Certain of these devices have incorporated a bionator which essentially spreads the jaw to permit the teeth to erupt to establish a new bite with a greater vertical height between the maxilla and mandible. However, none of the prior devices provided for incremental posterior movement of the mandible from an underbite position while permitting the molars to erupt to maintain an ultimate increased vertical height between the maxilla and mandible.

SUMMARY OF THE INVENTION

It is accordingly one object of the present invention to provide an improved method for recapturing an anteriorly displaced mandibular disc in an extremely efficient and expedient manner.

Another object of the present invention is to provide an improved functional jaw orthopedic device for recapturing an anteriorly displaced mandibular disc in an extremely efficient and expedient manner. Other objects and attendant advantages of the present invention will readily be perceived hereafter.

The method of recapturing an anteriorly displaced mandibular disc comprises the steps of moving the mandible to an anterior position from its normal position to increase the vertical height between the condyle and fossae, firmly retaining the mandible in said anterior position to permit said mandibular disc to become displaced to a more posterior position, periodically moving said mandible to a more posterior position in increments until it is returned to a permanent position which is anterior of its original normal position, and providing sufficient clearance between the lower and upper molars to permit eruption of certain of said molars during periodic movement of said mandible, to thereby maintain said increased vertical height.

The functional jaw orthopedic device of the present invention for recapturing an anterior displaced mandibular dics comprises a palatal body for fixed placement in the palate area in relation to the upper teeth, a mandibular body for fixed placement in the mandibular area in relation to the lower teeth, means for adjustably attaching said mandibular body to said palatal body for relative movement in a posterior direction from an underbite position, and a clearance area on said device in the area between the upper and lower molars to permit eruption for increasing the vertical spacing between the maxilla and the mandible to maintain the new condyle to fossae relationship.

The various aspects of the present invention will be more fully understood when the following portions of the present invention are read in conjunction with the accompanying drawings wherein:

BRIEF DESCRIPTION OF THE DRAWINGS

FIG. 5 is a plan view of the functional jaw orthopedic device of the present invention;

FIG. 6 is a side elevational view of the device of FIG. 5;

FIG. 7 is a view taken substantially in the direction of arrows 7—7 of FIG. 6 and is a front elevational view of the device of FIG. 5;

FIG. 8 is a view taken substantially in the direction of arrows 8—8 of FIG. 6 and is a rear elevational view of the device of FIG. 5;

FIG. 9 is a cross sectional view taken substantially along line 9—9 of FIG. 5 and showing the two sets of adjustment screws for both shifting the mandibular body portion relative to the palatable body portion and for spreading the anterior portion of the mandibular body portion;

FIG. 10 is an enlarged fragmentary cross sectional view taken substantially along line 10—10 of FIG. 9 and showing the construction of the adjusting screws for adjusting the width of the anterior portion of the mandibular body portion; and FIG. 11 is a fragmentary cross sectional view taken substantially along line 11—11 of FIG. 5 and showing the construction of the screws for adjusting the position of the mandibular body portion relative to the palatal body portion.

DESCRIPTION OF THE PREFERRED EMBODIMENTS

Figure 1:
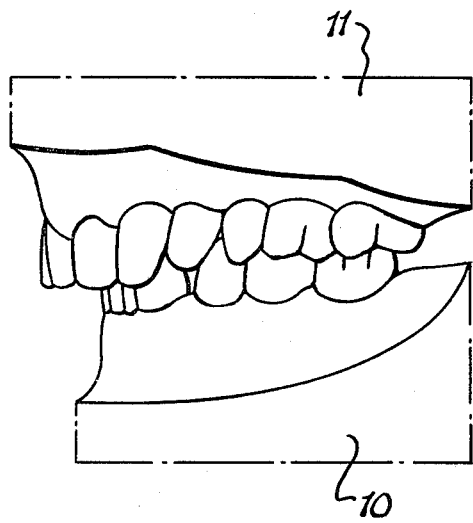
FIG. 1 is a side elevational view of the jaws with a person having an anterior displaced mandibular disc, with the jaws being in their normal position.
Figure 2:
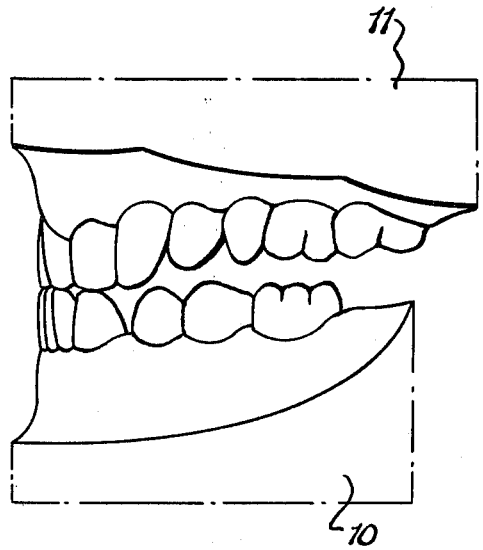
FIG. 2 is a side elevational view of the jaws of FIG. 1 with the mandible positioned anteriorly, in which position an impression is made for fabricating the functional jaw orthopedic device for recapturing the disc.
Figure 3:
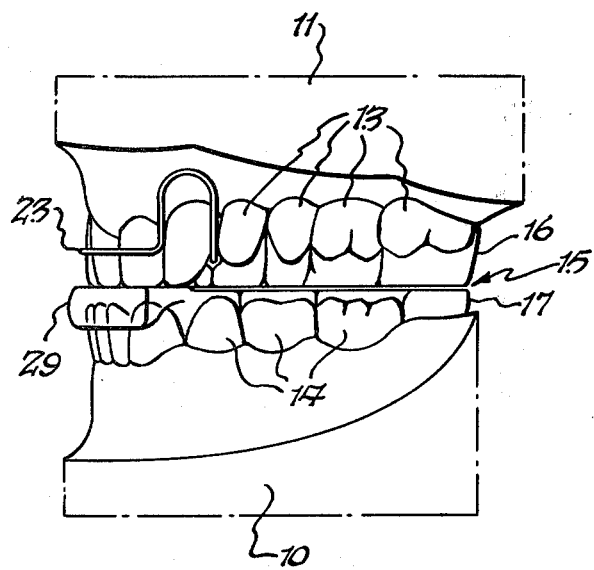
FIG. 3 is a side elevational view of the jaws with the functional jaw orthopedic device in position for retaining the mandible which is anterior to the normal position of FIG. 1 and which is approximately the position of FIG. 2.

The method of recapturing an anterior displaced mandibular disc is pictorially depicted in FIGS. 1-4. In accordance with this method, the mandible 10 is repositioned from its normal position relative to the maxilla 11 shown in FIG. 1 to the position shown in FIG. 2. When this is done, the vertical height between the mandible and maxilla is increased from the height shown in FIG. 1 to the height shown in FIG. 2. In this position an impression is made for the purpose of forming a functional jaw orthopedic device which is described in greater detail hereafter. The functional jaw orthopedic device is then worn by the patient, as shown in FIG. 3, for the purpose of maintaining the mandible and maxilla separated to the extent shown, and this will maintain the desired vertical height therebetween. By virtue of maintaining this relationship, the mandibular disc (not shown), which is located between the condyle of the mandible and the fossae of the maxilla at the temporal mandibular joint, will move posteriorly as a result of the normal muscular forces of a person.

Figure 4:
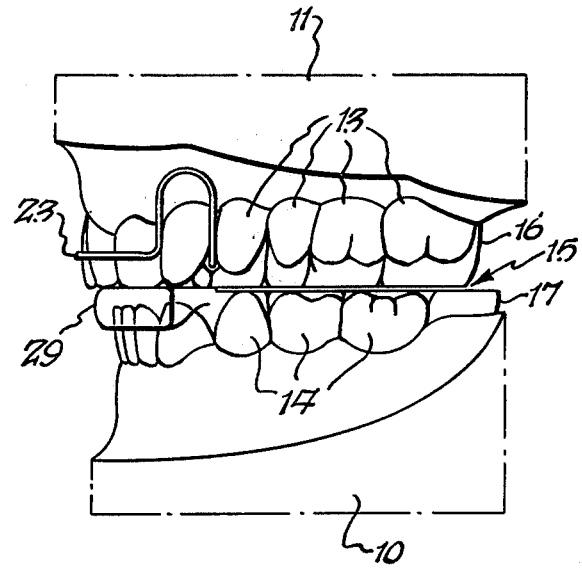
FIG. 4 is a view of the jaws with the functional jaw orthopedic device therebetween and with the latter adjusted to reposition the mandible posteriorly of the position of FIG. 3 but not as far back as the normal position of FIG. 1.

Thereafter, by adjusting the functional jaw orthopedic device in increments to a position such as shown in FIG. 4, the mandible will be positioned more posteriorly and the vertical height between the upper and lower molars will be decreased from the position shown in FIG. 3 to the position shown in FIG. 4. However, during the wearing of the device, which permits the upper molars 13 to be spaced from the lower molars 14, there will be relative eruption therebetween so that when the orthopedic device is no longer worn, the eruption of the molars will cause the vertical height between the mandible and the maxilla to be greater than the original height of FIG. 1. If desired, interproximal elastic ligatures may be used to increase the speed of eruption. Preferably the upper molars are blocked against eruption so that the entire eruption is of the lower molars. It is especially to be noted that the ultimate posterior positioning of the mandible is such that it never reaches the original normal position of FIG. 1. Thus the mandibular disc may be recaptured in a new position, and it will be retained therein after the orthopedic device is no longer being worn because the eruption of the molars will have increased the vertical height between the mandible and the maxilla. This will obviate the tendency for the mandibular disc to be displaced because of pressure between the condyle and fossae.

The functional jaw orthopedic device 15 of the present invention is shown in FIGS. 5–11. The device 15 includes a palatal body portion 16 and a mandibular body portion 17 which are secured to each other for relative horizontal movement by a pair of screw devices 19. The palatal and mandibular body portions are fabricated from an impression of the patient's oral cavity taken when the mandible is positioned anteriorly to the position of FIG. 2 from its normal position of FIG. 1.

The palatal body portion includes a right wing 20 and a left wing 21 which are optionally interconnected at their medial portions by means of a coffin spring 22. This spring not only serves the function of retaining the halves together, but may also be used for lateral expansion of the maxillary posterior teeth and may also be used in conjunction with myofunctional therapy. The anterior portions of the palatal wings 20 and 21 are interconnected by a labial bar 23. This bar is used mainly as a counterbalancing force opposing mandibular forces on the lower cap described hereafter. This enables the upper anterior teeth to remain in proper alignment during the procedure. The mandibular body portion 17 consists of right and left halves 24 and 25 which are connected by a screw device 26 to be described hereafter, or, if desired, the right and left halves 24 and 25 can be formed as an integral unit.

The palatal body portion, or maxillary arch, may incorporate a plastic cap for receiving the posterior maxillary teeth to prevent extrusion thereof. However, this modification is optional, and it is used only when extrusion of the upper maxillary teeth is to be prevented. It may be omitted from the palatal body portion if desired, in which event there would be some extrusion of the maxillary molars, or it may be incorporated into the palatal body portion initially and removed after a period of therapy so that there will be unequal extrusion of the maxillary and mandibular posterior teeth. In this respect, it is to be noted that there is no cap or obstruction on the mandibular body portions which would in any way impede eruption of the mandibular posterior teeth. As noted above, it is desired that this eruption should occur because of the fact that the ultimate objective of the therapy is to retain an increased vertical height between the mandible and the maxilla so as to hold the recaptured mandibular disc in its new position after therapy has been completed.

An acrylic cap, consisting of halves 27 and 29, which are essentially mirror image counterparts of each other, are formed on right and left halves 24 and 25, respectively. These caps cover the lower six anterior teeth in the anterior cap area and function as a guide for maintaining the proper mandibular position. The maintaining of the six anterior teeth in a precise position by the use of the caps 27 and 29 is essential for the function of recapturing the mandibular disc.

When the orthopedic device 15 is first worn, it is adjusted to the position shown in FIG. 3 wherein the mandible is in an anterior position. In this respect, it is to be noted that the screw adjusting mechanisms 19 between the upper and lower halves of the maxillary and mandibular portions include an anchor bar 30 having an upper portion 31 embedded in the upper half and a lower portion 32 received in cavity 33 in the lower half. Pins 34 and 35 extend through guideways 36 and 37 in lower portion 32, and the ends of these pins are anchored in brackets 39 and 40 which are embedded in lower halves 24 and 25. Because of the foregoing structure, member 30 can be moved in the direction of arrows 41 whenever screw 42 is rotated within tapped bore 43 in portion 32. This rotation is effected by inserting a pin into aperture 44 in boss 45 to thereby rotate screw 42, the screw having an end portion 46 journalled for rotation in bracket 39 but held against axial movement by boss 45 and cap 47 which bear against opposite sides of bracket 39. By the use of the above described screw devices 19, the mandibular body portion 20 can be moved both posteriorly and anteriorly relative to the maxillary portion to thereby make corresponding adjustments of the mandible.

When the functional jaw orthopedic device is initially installed, a slight anterior or posterior adjustment is effected by the use of adjusters 19 so as to place the mandible in the position of FIG. 3. Thereafter, the mandible is moved posteriorly in increments by adjusting screw devices 19 slightly until the mandible reaches the position of FIG. 4. There may be as many as four or five adjustments between the positions of FIGS. 3 and 4, each at about six-week intervals, to permit the mandibular disc to be recaptured. As noted above, during this period, in view of the increased vertical height between the mandible and maxilla, the lower molars, and optionally the upper molars as described above, may erupt so that when the therapy has been completed and the device 15 is no longer being worn after the mandible has reached the position of FIG. 4, the erupted molars will maintain the desired vertical height which will cause the mandibular disc to be retained in its recaptured position.

The screw adjuster 26 between the mandibular halves 24 and 25 is shown in enlarged detail in FIG. 10. Adjuster 26 includes a first bracket portion 49 embedded in mandibular body half 24 and a second bracket portion 50 embedded in mandibular body half 25. Pin 51 extends through bores 52 and 53 in bracket portions 49 and 50, respectively. Pin 54 extends through bores 55 and 56 in bracket portions 49 and 50, respectively. A turnbuckle 57 has threads of opposite hand on portions 59 and 60 thereof which are threaddedly received in brackets 49 and 50, respectively. A head 61 having an aperture 62 for receiving a wrench is centrally located on the turnbuckle 57, and when head 61 and screws 59 and 60 are rotated, brackets 49 and 50 will either be drawn together or apart. By thus moving the mandibular halves 24 and 25 toward or away from each other, the spacing of the anterior mandibular teeth may be varied.

It will be appreciated that the basic device essentially comprises the palatal and mandibular body portions interconnected for relative anterior and posterior movement, with the mandibular portion being cut away in the molar area to permit eruption of the posterior mandibular molars and having an anterior cap for guiding the proper mandibular position. In addition, as noted above, the specific embodiment discloses the use of a coffin spring 22 and a labial bar 23 and also incorporated a screw adjustment between the anterior mandibular halves. If desired, there can be incorporated sagittal expansion screws and mid-palatal screws when needed. In the event that mid-palatal screws are used, they must be activated first. The labial lingual movement must be corrected before the saggital correction is made. Saggital screws can next be activated. The repositioning of the anterior teeth forward should be done before second molars are extracted. If distillization of the posterior segment (first premolar to the first molar) is indicated, second molars should be extracted prior to the activation of the sagittal screws. Cuspid retraction wires can be placed in these devices as required. The labial bow may or may not be added to the sagittal component depending again on requirements. Obviously the lingual wire and the coffin spring, as described above, are eliminated.

Other known structures can be incorporated into the device 15. For example, there can be a combination of modalities for Class 3 malocclusions. Such a device would include a saggital component while having a lower component such as shown in FIG. 10. This combination enables the maxillary teeth to be flared anteriorly while the mandible is being retracted posteriorly. This combination would be used in tandem with a face bow and heavy elastics to the maxilla. When these three components (saggital, elastics with face bow, and posteriorization of the mandible) are used together, a rapid clinical result can be anticipated. The foregoing modifications of the basic structure have been described by way of example and not of limitation, it being understood that other conventional modifications may be incorporated into the basic functional jaw orthopedic device described above for the purpose of remedying existing problems in a known manner in conjunction with the recapturing of the anteriorly displaced mandibular disc as described above.

While preferred embodiments have been disclosed, it will be appreciated that the present invention is not limited thereto but may be otherwise embodied within the scope of the following claims.

What is claimed is:

1. A method of recapturing an anterior displaced mandibular disc comprising the steps of moving the mandible to an anterior position from its normal position to increase the vertical height between the condyle and fossae, firmly retaining the mandible in said anterior position to permit said mandibular disc to become displaced to a more posterior position, periodically moving said mandible to a more posterior position in increments until it is returned to a permanent position which is anterior to its original normal position, and providing sufficient clearance between the lower and upper molars to permit eruption of certain of said molars during said periodic movement of said mandible, to thereby cause said erupted molars to maintain the increased vertical height.

2. A method as set forth in claim 1 including placing a cap over the lower anterior teeth for guiding the proper mandibular position.

3. A method as set forth in claim 2 wherein said clearance is only for the lower molars.

4. A method of recapturing an anterior displaced mandibular disc comprising the steps of mounting a palatal body in firm relationship to the maxilla, mounting a mandibular body which is connected to the palatal body in firm relationship to the mandible so that the mandible is maintained in an anterior position from its normal position to increase the vertical height between the condyle and fossae, periodically moving said mandible posteriorly in increments by moving said mandibular body posteriorly in increments relative to said palatal body to permit said mandibular disc to be displaced to a more posterior position, and terminating said posterior incremental movement of said mandibular body at a position which is anterior to its original normal position.

5. A method as set forth in claim 4 including the step of providing sufficient clearance between the upper and lower molars to permit eruption of certain of said molars during said periodic movement of said mandibular body, to thereby cause said erupted molars to maintain said increased vertical height.

6. A method as set forth in claim 5 wherein said clearance is only for the lower molars.

7. A method as set forth in claim 5 including the step of placing a cap on said mandibular body over the lower anterior teeth for guiding the proper position of said mandible.

8. A method as set forth in claim 4 including the step of placing a cap on said mandibular body over the lower anterior teeth for guiding the proper position of said mandible.

9. A functional jaw orthopedic device for recapturing an anterior displaced mandibular disc by moving a mandible anteriorly to an underbite position from a normal posterior position and thereafter moving said mandible in increments to a final position which is anterior of said normal posterior position comprising a palatal body for fixed placement in the palate area in relation to the upper teeth, a mandibular body for fixed placement in the mandibular area in relation to the lower teeth, means for adjustably attaching said mandibular body to said palatal body for relative movement in increments in a posterior direction from an underbite position to reposition a mandible posteriorly from said underbite position to said final position, and a clearance area on said device in the area between the upper and lower molars to permit eruption of certain of said molars for increasing the vertical spacing between the temporal bone and the mandible in the condyle-fossae area to retain said mandible in said final position wherein said mandibular disc has been recaptured.

10. A functional jaw orthopedic device as set forth in claim 9 wherein said attachment means includes means for effecting said adjustment in both an anterior and posterior direction.

11. A functional jaw orthopedic device as set forth in claim 9 including guide means on said mandibular body for guiding said mandible to a proper position.

12. A functional jaw orthopedic device as set forth in claim 11 wherein said guide means comprise a cap for placement over the lower anterior teeth.

13. A functional jaw orthopedic device as set forth in claim 12 wherein said clearance area is on said mandibular body for permitting eruption of said lower molars.

14. A functional jaw orthopedic device as set forth in claim 9 wherein said clearance area is on said mandibular body for permitting eruption of said lower molars.

* * * * *